United States Patent [19]

Samson et al.

[11] Patent Number: 4,597,755

[45] Date of Patent: Jul. 1, 1986

[54] LARGE BORE CATHETER HAVING FLEXIBLE TIP CONSTRUCTION

[75] Inventors: Wilfred J. Samson, Saratoga; Deepak R. Gandhi, San Jose, both of Calif.

[73] Assignee: Advanced Cardiovascular Systems, Inc., Mountain View, Calif.

[21] Appl. No.: 615,140

[22] Filed: May 30, 1984

[51] Int. Cl.[4] ............................................. A61M 25/00
[52] U.S. Cl. ..................................... 604/96; 604/103; 604/280
[58] Field of Search ..................................... 604/96–103, 604/282, 280, 281, 283; 128/344

[56] References Cited

U.S. PATENT DOCUMENTS

| 623,022 | 4/1899 | Johnson | 604/280 X |
| 3,913,565 | 10/1975 | Kawahara | 604/96 X |
| 4,276,874 | 7/1981 | Wolvek et al. | 604/96 |
| 4,307,722 | 12/1981 | Evans | 128/344 |
| 4,444,188 | 4/1984 | Bazeu et al. | 604/97 X |
| 4,498,473 | 2/1985 | Gereg | 604/96 X |

FOREIGN PATENT DOCUMENTS 823320 12/1951 Fed. Rep. of Germany ...... 604/282

*Primary Examiner*—Stephen C. Pellegrino
*Attorney, Agent, or Firm*—Flehr, Hohbach Test, Albritton & Herbert

[57] ABSTRACT

Large bore catheter having a flexible tip construction. A main flexible shaft tube is provided having a flow passage therein and having proximal and distal ends. A coil spring is secured to the distal end of the main shaft tube. Flexible tubing extends over the exterior of the coil spring and has a distal extremity which extends beyond the distal extremity of the coil spring. The flexible tubing forms a close fit over the coil spring.

7 Claims, 2 Drawing Figures

U.S. Patent     Jul. 1, 1986     4,597,755
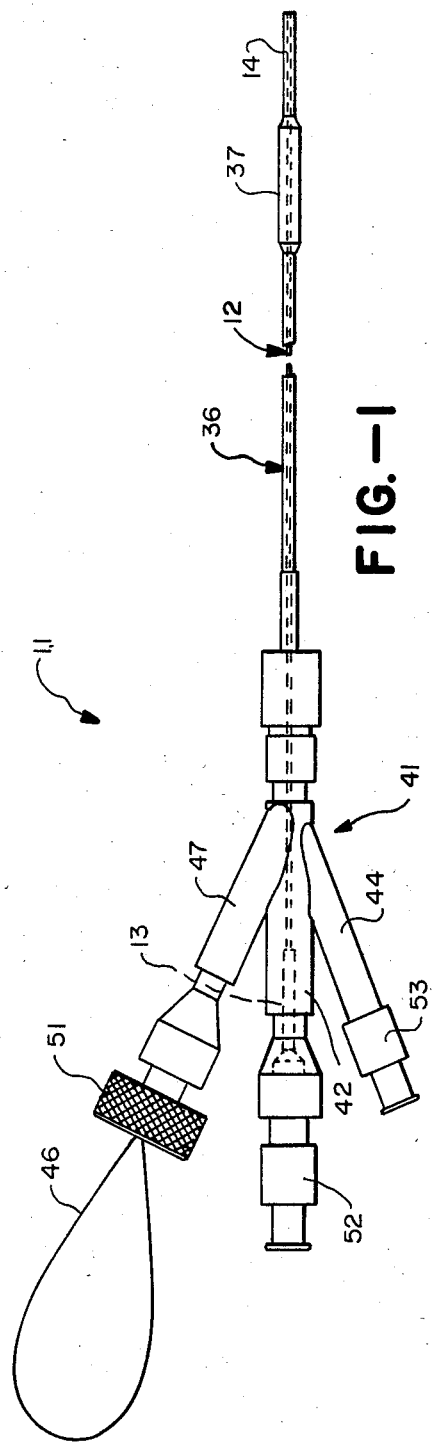
FIG.—1
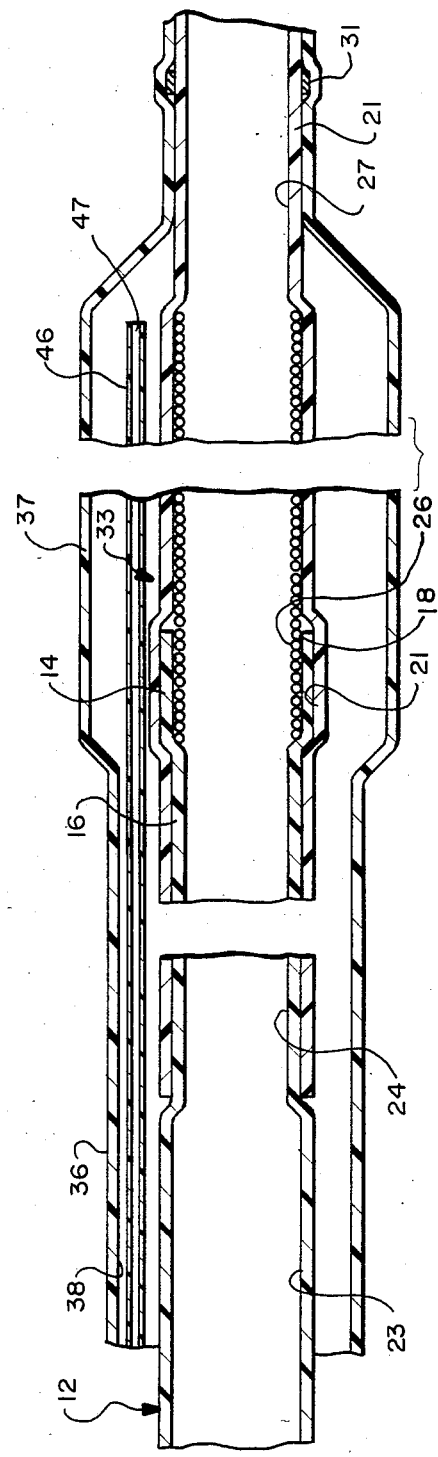
FIG.—2

LARGE BORE CATHETER HAVING FLEXIBLE TIP CONSTRUCTION

This invention relates to catheters having flexible tips and more particularly to large bore catheters having flexible tips.

Catheters having flexible tips have heretofore been provided. However, such catheters generally have been of relatively small bores. It has been found that when catheters are provided with larger bores and with relatively smaller wall thickness, the tips have a tendency to kink making it difficult, if not impossible, to perform certain operations such as moving guide wires, making dye injections and making pressure measurements. There is therefore a need for a new and improved large bore catheter which has flexible tips which will overcome these difficulties.

In general it is an object of the present invention to provide a large bore catheter having a flexible tip which is kink resistant.

Another object is to provide a catheter of the above character which can accommodate acute bends and reach tortuous vessels and branches.

Another object of the invention is to provide a catheter of the above character in which the tip of the catheter can track guide wires easily.

Another object of the invention is to provide a catheter of the above character in which a coil spring is utilized to provide the kink resistance and which also serves as a radioopaque marker to provide visualization during fluoroscopy.

Another object of the invention is to provide a catheter of the above character which can be readily constructed.

Additional objects and features of the invention will appear from the following description in which the preferred embodiments are set forth in detail in conjunction with the accompanying drawing.

FIG. 1 is a side elevational view partially in cross section, a part of which is enlarged, of a large bore catheter having a flexible tip construction incorporating the present invention.

In general the large bore catheter having a flexible tip construction is comprised of a main shaft having a flow passage extending therethrough and which is provided with proximal and distal ends. A coil spring is secured to the distal end of the main shaft. A flexible plastic tube extends over the coil spring and has a distal extremity extending beyond the distal extremity of the coil spring. An additional flexible tube extends over the distal end of the main shaft and over the flexible plastic tube extending over the coil spring and has a balloon formed therein near the distal extremity of the coil spring. The distal extremity of the additional tube is bonded to the flexible tube. A fitting is provided which is secured to the proximal ends of the main flexible shaft and the additional tube whereby a radiopaque contrast liquid can be introduced into the balloon to permit visualization of the balloon under fluoroscopy.

More particularly as shown in FIG. 1, the large or big bore catheter 11 having a flexible tip construction consists of a main shaft tube 12. The main shaft tube 12 is formed of a suitable material. It preferably is relatively stiff and can be formed of suitable medical grade material such as polyolefins, polyvinyl chloride and other suitable medical grade polymeric materials. It can have suitable dimensions such as 0.027 inside diameter and 0.037 inches outside diameter ±20%. The main shaft tube 12 is provided with proximal and distal extremities 13 and 14. The main shaft tube 12 adjacent the distal extremity 14 is provided with a necked down region 16 which is of smaller diameter. This necking down can be accomplished by inserting a smaller suitable mandrel such as 0.024 inches and heating the region while the tubing is under tension. After this has been accomplished the mandrel can be removed.

A coil spring 18 is provided. The coil spring 18 can be formed of any suitable material, however, it preferably should have a high modulus and should have a high density. Suitable materials are platinum, tungsten and tantalum, preferably in alloy form to give the desired spring characteristics. The coil spring can be formed from a ribbon material which has a rectangular cross section or alternatively, from a wire which is cylindrical in cross section. The coil spring can have a suitable length such as 25 millimeters ±½ millimeter. The coil spring 18 is tightly wound so that each coil is immediately adjacent to the next coil. One end of the coil spring 18 is inserted into the distal extremity of the main shaft tube 12. By way of example, this can be accomplished by placing the coil spring 18 on a mandrel of a suitable size, as for example, a mandrel having a diameter of 0.021 inches. The mandrel with the spring thereon then can be inserted into the distal extremity of the main shaft tube 12 which has an opening of a suitable size, as for example, 0.024 inches.

A piece of flexible tubing 21 having a larger diameter is then inserted over the coil spring 18 and extends over the distal extremity of the main shaft tube 12 and over the necked-down region 16 as shown particularly in FIG. 1. This tubing 21 can be formed of a suitable flexible material such as polyolefins and other suitable medical polymeric materials.

After the assembly has been made up to the point herein described in which the tubing 21 extends over the coil spring 18 and over the distal extremity of the main shaft tube 12, the entire length of the tubing 21 is heated in a suitable manner such as by a heat gun to shrink the tubing 21 beginning with the portion overlying the region 16 and extending distally to the distal extremity of the tubing 21 to cause it to shrink down onto the spring and the mandrel carrying the spring 18 as, for example, down to a diameter of 0.021 inches so that there is a relatively smooth transition between the passageway 23 provided in the main shaft tube 12, and the passageway 24 provided in the necked-down region 16 of the main shaft tube 12. The passageway 24 is generally in alignment with a passageway 26 provided in the coil spring 18 and also is in general alignment with the passageway 27 provided in the distal extremity of the tubing 21. The shrink operation causes a close fit to be formed between the coil spring 18 and the intrior of the tubing 21. After the shrinking operation has been completed, the distal extremity of the tubing 21 is cut to an appropriate length.

A band 31 of a suitable radiopaque material such as gold is put over the tip or distal extremity of the tubing 21 as described in copending application Ser. No. 522,820 filed Aug. 12, 1983. This completes an inner assembly for the catheter 11.

Therafter, a length of outer or balloon tubing 36 is provided which also can be formed of the flexible material hereinbefore described, as for example, Polyolefins, polyvinylchloride and others, which has a balloon 37 formed as an integral part of the tubing 36. Typically the balloon 37 is sized in such a manner so that it is generally co-extensive in length with respect to the length of the coil spring 18. It can have a diameter such as 2 or 3 millimeters. The balloon tubing 36 is then positioned over the inner assembly 33 hereinbefore described so that the balloon 37 is in general registration with the coil spring 18 as shown in FIG. 1. The distal extremity of the balloon tubing 36 is then sealed to the distal extremity of the inner assembly 33 formed by the tubing 21 in a suitable manner such as by the use of the application of heat to the balloon tubing 36 to form a liquid-tight seal between the tubing 31 and the distal extremity of the inner assembly 33. The tubing 36 extends to the proximal extremity of the main shaft tubing 12. There is provided an annular passageway 38 between the interior of the tubing 36 and the exterior of the tube 21 and the main shaft tube 12 and extending from the balloon 37 to the proximal extremity of the tubing 36.

A three-arm adapter or fitting 41 is mounted on the proximal extremity of the main shaft tube 12 and the tubing 36. The three-arm adapter 41 is provided with a central arm 42 and side arms 43 and 44. The main shaft 12 is connected to the central arm 42 whereas the balloon tubing 36 is connected to the side arms 43 and 44. A balloon flushing wire or tube 46 is mounted in the side arm 43 and extends through the passage 38 into the distal extremity of the balloon 37 as shown in FIG. 1. The balloon flushing wire 46 is provided with a passage 47 which extends the length thereof. The fitting 43 is provided with an O-ring (not shown) which is adapted to be compressed by a screw 49 carrying a knurled knob 51 in a manner well known to those skilled in the art to form a liquid-tight seal between the flushing wire 46 and the side arm 43. The central arm 42 and the side arm 44 are provided with Leuer-type fittings 52 and 53.

The catheter assembly hereinbefore described can be used in a conventional manner well known to those skilled in the art for insertion into blood vessels and branches. A radiographic contrast liquid can be introduced into the side arm 44 to cause inflation of the balloon outside of the vessel to see that the balloon properly inflates and so that all of the air within the balloon is forced out through the balloon flushing tube or wire 46. After all the air has been removed, the flushing wire 46 can be bent back onto itself with the proximal extremity of the same inserted back into the arm 43 and clamped into the O-ring to close off the passage 47 in the balloon flushing wire. The central passageway 23 provided in the main shaft 12 can be utilized for the introduction of guide wires which can be used to facilitate insertion of the catheter. It also can be utilized for inserting dyes and making pressure measurements.

In use, it has been found that the catheter construction hereinbefore described is particularly useful for large bore applications as, for example, heart, lung and renal catheters. Sharp bends can be readily accommodated without kinking. This makes it possible to pass a guide wire through the catheter and to move the guide wire when the catheter is in place. The catheter also makes it possible to make distal dye injections and pressure measurements.

It is apparent from the foregoing that there has been provided a new and improved large bore catheter which has a flexible tip construction which makes it possible to negotiate acute bends without danger of kinking. It is constructed in such a manner so that it can be readily fabricated with conventional materials.

What is claimed is:

1. In a large bore catheter tube having a flexible tip construction, a main flexible shaft tube having proximal and distal ends and having a flow passage extending therethrough, a coil spring secured to the distal end of the main shaft tube, and flexible tubing extending over the exterior of the coil spring and having a distal extremity which extends beyond the distal extremity of the coil spring, the flexible tubing forming a close fit over the coil spring, the flexible tubing in conjunction with the coil spring providing an additional passage which adjoins and is in communication with the first named flow passage.

2. A catheter as claimed in claim 1 wherein there is a relatively smooth transition between the first named and additional passageways in the main flexible shaft tube and in the coil spring.

3. A catheter as in claim 1 wherein the proximal extremity of the coil spring is disposed within the interior of the distal extremity of the main shaft tube and wherein the flexible tubing extends over the distal extremity of the main shaft tube.

4. In a large bore catheter tube having a flexible tip construction, a main flexible shaft tube having proximal and distal ends and having a flow passage extending therethrough, a coil spring secured to the distal end of the main shaft tube, flexible tubing extending over the exterior of the coil spring and having a distal extremity which extends beyond the distal extremity of the coil spring, the flexible tubing forming a close fit over the coil spring and a balloon tubing formed of a flexible material extending coaxially from the distal extremity of the flexible tubing and the proximal extremity of the main shaft tube, said balloon tubing having a balloon carried thereby which is substantially co-extensive in length with the coil spring, the distal extremity of the balloon tubing being sealed to the distal extremity of the flexible tubing, the balloon tubing providing a flow passage extending from the balloon to the proximal extremity of the main flexible shaft tube.

5. A catheter as in claim 4 wherein said main shaft tube, said flexible tubing and said balloon tubing are formed of heat shrinkable plastic materials.

6. A catheter as in claim 4 together with a three-arm adapter secured to the proximal extremity of the main flexible shaft tube and to the proximal extremity of the balloon tubing with one of the arms being in communication with the passageway in the main shaft tubing and another of the arms being in communication with the passageway leading to the balloon.

7. In a large bore catheter tube having a flexible tip construction, a main flexible shaft tube having proximal and distal ends and having a flow passage extending therethrough, a coil spring secured to the distal end of the main shaft tube, and flexible tubing extending over the exterior of the coil spring and having a distal extremity which extends beyond the distal extremity of the coil spring, the flexible tubing forming a close fit over the coil spring, the flexible tubing in conjunction with the coil spring providing an additional passage which adjoins and is in communication wtih the first named flow passage, said coil spring being formed of a material which is relatively opaque to x-rays.

* * * * *